US009402763B2

(12) United States Patent  
Bledsoe

(10) Patent No.: US 9,402,763 B2  
(45) Date of Patent: Aug. 2, 2016

(54) COLD THERAPY APPARATUS HAVING HEAT EXCHANGING THERAPY PAD

(75) Inventor: Gary R. Bledsoe, Mansfield, TX (US)

(73) Assignee: Breg, Inc., Carlsbad, CA (US)

( * ) Notice: Subject to any disclaimer, the term of this patent is extended or adjusted under 35 U.S.C. 154(b) by 922 days.

(21) Appl. No.: 13/611,807

(22) Filed: Sep. 12, 2012

(65) Prior Publication Data

US 2014/0074198 A1    Mar. 13, 2014

(51) Int. Cl.
*A61F 7/00* (2006.01)
*A61F 7/10* (2006.01)
*A61F 7/02* (2006.01)

(52) U.S. Cl.
CPC ........... *A61F 7/10* (2013.01); *A61F 2007/0056* (2013.01); *A61F 2007/0244* (2013.01); *A61F 2007/0257* (2013.01); *A61F 2007/0268* (2013.01); *A61F 2007/0273* (2013.01); *A61F 2007/0274* (2013.01)

(58) Field of Classification Search
CPC .............. A61F 7/10; A61F 2007/0056; A61F 2007/0244; A61F 2007/0246; A61F 2007/0268; A61F 2007/0273; A61F 2007/0274

See application file for complete search history.

(56) References Cited

U.S. PATENT DOCUMENTS

| | | |
|---|---|---|
| 222,690 A | 12/1879 | Goldschmidt |
| 1,896,953 A | 5/1931 | Hassell |
| 2,260,134 A | 10/1939 | Ballman |
| 2,726,658 A | 12/1955 | Chesseu |
| 3,316,732 A | 5/1967 | Burton |
| 3,587,577 A | 6/1971 | Smirnov |
| 3,648,765 A | 3/1972 | Starr |
| 3,744,555 A | 7/1973 | Fletcher |
| 3,811,431 A | 5/1974 | Apstein |
| 3,892,229 A | 7/1975 | Taylor |
| 3,901,221 A | 8/1975 | Nicholson |
| 3,918,458 A | 11/1975 | Nethery |
| 3,942,518 A | 3/1976 | Ternterus |
| 3,967,627 A | 7/1976 | Brown |

(Continued)

FOREIGN PATENT DOCUMENTS

| | | |
|---|---|---|
| CA | 2601496 | 3/2008 |
| EP | 2275164 | 1/2001 |

(Continued)

OTHER PUBLICATIONS

Orthofix International, "Orthofix International Introduces FUSION lateral OA Brance with New Low-Profile Hinge," News Blaze, published Dec. 4, 2009, http://newsblaze.com/story/2009120405052100002.bw/topstory.html.

(Continued)

*Primary Examiner* — Kaitlyn Smith
(74) *Attorney, Agent, or Firm* — K&L Gates LLP

(57) ABSTRACT

A cold therapy system includes (i) a cooling bath structured to chill and hold chilled water; (ii) a pump positioned and arranged to pump the chilled water; (iii) a to-pad line positioned and arranged to hold chilled water pumped by the pump from the cooling bath; (iv) a from-pad line positioned and arranged to hold water returning to the cooling bath; and (v) a therapy pad in fluid communication with the to- and from-pad lines, the therapy pad including a patient-contacting chamber that is in heat exchange communication with a chilled-water chamber residing outside of the patient-contacting chamber when the therapy pad is donned.

24 Claims, 3 Drawing Sheets

(56) References Cited

U.S. PATENT DOCUMENTS

| | | |
|---|---|---|
| 3,971,398 A | 7/1976 | Taylor |
| 3,993,053 A | 11/1976 | Grossan |
| 4,013,069 A | 3/1977 | Hasty |
| 4,030,488 A | 6/1977 | Hasty |
| 4,149,529 A | 4/1979 | Copeland |
| 4,156,425 A | 5/1979 | Arkans |
| 4,186,732 A | 2/1980 | Christoffel |
| 4,198,961 A | 4/1980 | Arkans |
| 4,202,325 A | 5/1980 | Villari |
| 4,206,751 A | 6/1980 | Schneider |
| 4,207,875 A | 6/1980 | Arkans |
| 4,253,449 A | 3/1981 | Arkans |
| 4,306,747 A | 12/1981 | Moss |
| 4,311,135 A | 1/1982 | Brueckner |
| 4,370,975 A | 2/1983 | Wright |
| 4,375,217 A | 3/1983 | Arkans |
| 4,396,010 A | 8/1983 | Arkans |
| 4,453,538 A | 6/1984 | Whitney |
| 4,501,126 A | 2/1985 | Norton |
| 4,694,521 A | 9/1987 | Tominaga |
| 4,773,494 A | 9/1988 | Anderson |
| 4,821,354 A | 4/1989 | Little |
| 4,841,956 A | 6/1989 | Gardner |
| 4,844,702 A | 7/1989 | Ceccherini |
| 4,966,145 A | 10/1990 | Kikumoto |
| 5,022,387 A | 6/1991 | Hasty |
| 5,109,832 A | 5/1992 | Proctor |
| 5,186,163 A | 2/1993 | Dye |
| 5,218,954 A | 6/1993 | van Bennelen |
| 5,241,951 A * | 9/1993 | Mason et al. ............ 607/104 |
| 5,241,958 A | 9/1993 | Noeldner |
| 5,261,482 A | 11/1993 | Lomax |
| 5,263,473 A | 11/1993 | McWhorter |
| 5,330,519 A * | 7/1994 | Mason et al. ............ 607/104 |
| 5,383,894 A | 1/1995 | Dye |
| 5,496,262 A | 3/1996 | Johnson, Jr. |
| 5,507,792 A * | 4/1996 | Mason et al. ............ 607/104 |
| 5,588,955 A | 12/1996 | Johnson, Jr. |
| 5,626,556 A | 5/1997 | Tobler |
| 5,647,051 A * | 7/1997 | Neer ........................ 388/811 |
| 5,669,872 A | 9/1997 | Fox |
| 5,843,007 A | 12/1998 | McEwen |
| 5,865,841 A | 2/1999 | Kolen |
| 5,951,502 A | 9/1999 | Peeler |
| 5,980,561 A | 11/1999 | Kolen |
| 5,989,285 A | 11/1999 | DeVilbiss |
| 6,007,559 A | 12/1999 | Arkans |
| 6,080,120 A | 6/2000 | Sandman |
| 6,129,688 A | 10/2000 | Arkans |
| 6,146,411 A | 11/2000 | Noda et al. |
| 6,290,662 B1 | 9/2001 | Morris |
| 6,296,617 B1 | 10/2001 | Peeler |
| 6,358,219 B1 | 3/2002 | Arkans |
| 6,387,065 B1 | 5/2002 | Turney |
| 6,436,064 B1 | 8/2002 | Kloecker |
| 6,440,093 B1 | 8/2002 | McEwen |
| 6,447,467 B1 | 9/2002 | Barak |
| 6,463,612 B1 | 10/2002 | Potter |
| 6,463,934 B1 | 10/2002 | Johnson, Jr. |
| 6,478,757 B1 | 11/2002 | Barak |
| 6,494,852 B1 | 12/2002 | Barak |
| 6,544,202 B2 | 4/2003 | McEwen |
| 6,589,194 B1 | 7/2003 | Calderon |
| 6,592,534 B1 | 7/2003 | Rutt |
| 6,685,661 B2 | 2/2004 | Peled |
| 7,044,924 B1 | 5/2006 | Roth |
| 7,063,676 B2 | 6/2006 | Barak |
| 7,191,798 B2 | 3/2007 | Edelman |
| 7,207,959 B1 | 4/2007 | Chandran |
| 7,211,104 B2 | 5/2007 | Edelman |
| 7,282,038 B2 | 10/2007 | Gillis |
| 7,354,410 B2 | 4/2008 | Perry |
| 7,637,879 B2 | 12/2009 | Barak |
| 7,641,623 B2 | 1/2010 | Biondo |
| 7,658,205 B1 | 2/2010 | Edelman |
| 7,694,693 B1 | 4/2010 | Edelman |
| 7,708,707 B2 | 5/2010 | Cook |
| 7,819,829 B1 | 10/2010 | Chandran |
| 7,862,525 B2 | 1/2011 | Carkner |
| 7,871,387 B2 | 1/2011 | Tordella |
| 7,896,823 B2 | 3/2011 | Mangrum |
| 7,909,783 B2 | 3/2011 | Mayer |
| 7,909,861 B2 | 3/2011 | Balachandran |
| 7,931,606 B2 | 4/2011 | Meyer |
| 7,942,838 B2 | 5/2011 | Farrow |
| 7,959,588 B1 | 6/2011 | Wolpa |
| 7,967,766 B2 | 6/2011 | Ravikumar |
| 2001/0039439 A1 | 11/2001 | Elkins |
| 2008/0058911 A1 | 3/2008 | Parish |
| 2008/0077063 A1 | 3/2008 | Meyer |
| 2009/0069731 A1 | 3/2009 | Parish |
| 2009/0124944 A1 | 5/2009 | Ravikumar |
| 2009/0223518 A1 | 9/2009 | Kwok et al. |
| 2009/0293887 A1 | 12/2009 | Wilkes |
| 2009/0299249 A1 | 12/2009 | Wilkes |
| 2009/0299256 A1 | 12/2009 | Barta |
| 2009/0299257 A1 | 12/2009 | Long |
| 2009/0299307 A1 | 12/2009 | Barta |
| 2009/0299308 A1 | 12/2009 | Kazala |
| 2009/0299340 A1 | 12/2009 | Kazala |
| 2009/0299341 A1 | 12/2009 | Kazala |
| 2009/0299342 A1 | 12/2009 | Cavanaugh |
| 2010/0030306 A1 | 2/2010 | Edelman |
| 2010/0100017 A1 | 4/2010 | Maguina |
| 2010/0106229 A1 * | 4/2010 | Gammons et al. ............ 607/104 |
| 2010/0137764 A1 | 6/2010 | Eddy |
| 2010/0210982 A1 | 8/2010 | Balachandran |
| 2010/0249679 A1 | 9/2010 | Perry |
| 2011/0015587 A1 | 1/2011 | Turney |
| 2011/0015589 A1 | 1/2011 | Svedman |
| 2011/0015590 A1 | 1/2011 | Svedman |
| 2011/0077723 A1 | 3/2011 | Parish |
| 2011/0082401 A1 | 4/2011 | Iker |
| 2011/0092927 A1 | 4/2011 | Wilkes |
| 2011/0093050 A1 | 4/2011 | Damkoehler |
| 2011/0152796 A1 | 6/2011 | Kazala |
| 2011/0166480 A1 | 7/2011 | Mayer |
| 2011/0178481 A1 | 7/2011 | Locke |
| 2011/0190675 A1 | 8/2011 | Vess |
| 2011/0196269 A1 | 8/2011 | Arkans |
| 2011/0257573 A1 | 10/2011 | Hong |
| 2011/0275983 A1 | 11/2011 | Quisenberry |
| 2012/0065715 A1* | 3/2012 | Carson ............ A61F 7/10 607/104 |
| 2012/0158103 A1 | 6/2012 | Bledsoe et al. |
| 2012/0172957 A1* | 7/2012 | Dewaegenaere ............ 607/104 |
| 2014/0214138 A1* | 7/2014 | Voorhees et al. ............ 607/104 |

FOREIGN PATENT DOCUMENTS

| | | |
|---|---|---|
| EP | 1990039 | 11/2008 |
| FR | 2696342 | 4/1994 |
| GB | 2465712 | 2/2009 |
| IE | S950163 | 12/1995 |
| WO | 2005037154 | 4/2005 |
| WO | 2009158131 | 12/2009 |
| WO | 2011090986 | 7/2011 |

OTHER PUBLICATIONS

Breg Incorporated, "Fusion OA," published 2009, http://www.breg.com/knee-braceing/oa/fusion-oa.html.
Bledsoe Brace Systems, "Bledsoe Cold Control," published 2008, http//bledsoebrace.com/products/cold_control.asp.
International Search Report for PCT/US2013/059208 dated Dec. 19, 2013—3 pages.
Written Opinion for PCT/US2013/059208 dated Dec. 19, 2013—5 pages.

* cited by examiner

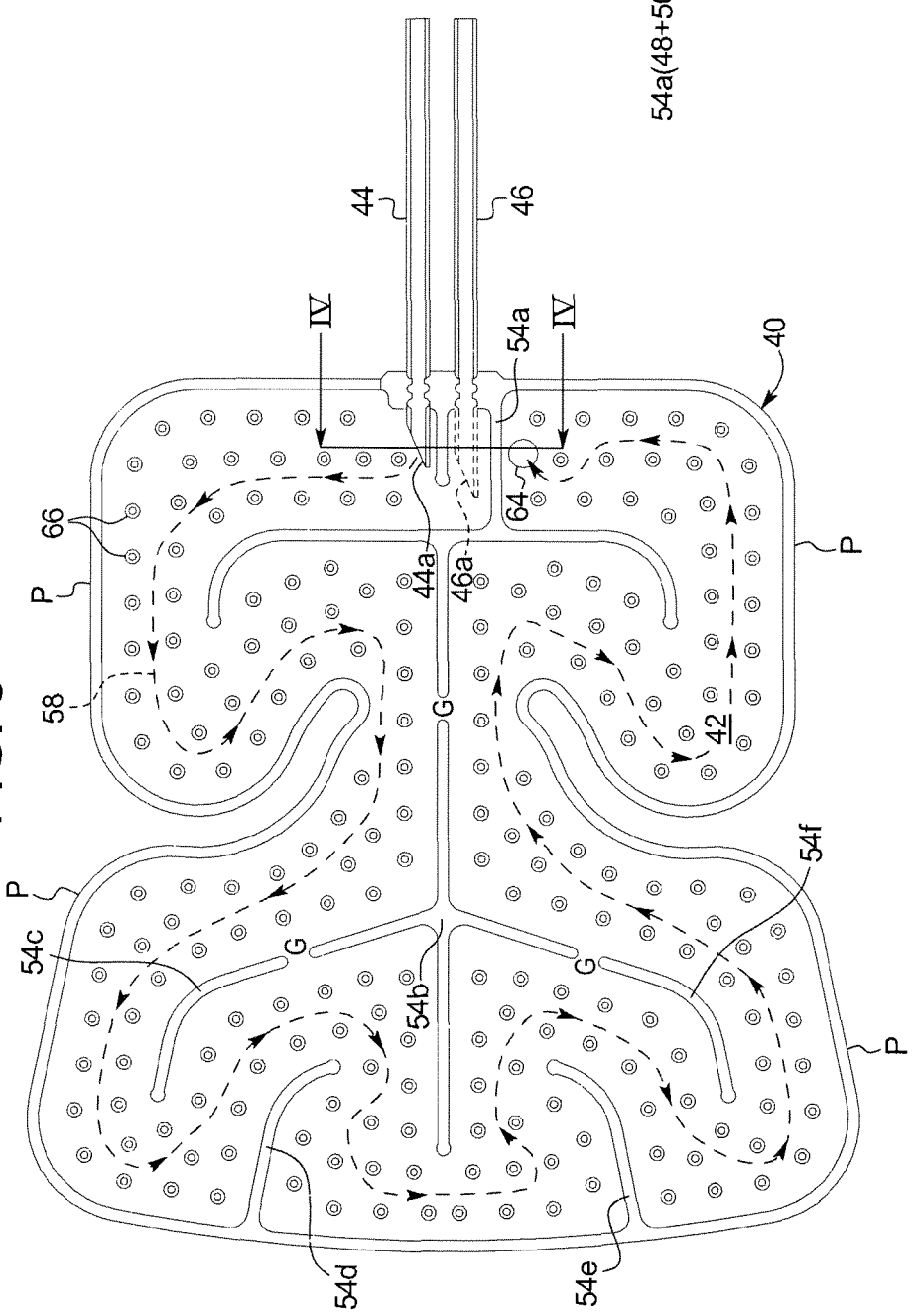
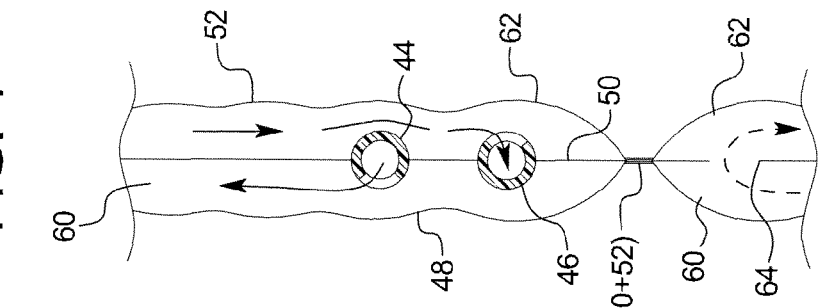

COLD THERAPY APPARATUS HAVING HEAT EXCHANGING THERAPY PAD

CROSS-REFERENCE TO RELATED APPLICATIONS

The present application is related by subject matter to commonly owned U.S. patent application Ser. No. 12/973,476 ("the '476 Application"), now U.S. Pat. No. 8,613,762 entitled, "Cold Therapy Apparatus Using Heat Exchanger", filed Dec. 20, 2010; U.S. patent application Ser. No. 13/418,857, entitled, "Cold Therapy Systems And Methods", filed Mar. 13, 2012; and U.S. patent application Ser. No. 13/419,022 ("the '022 Application"), now U.S. Pat. No. 9,114,055 entitled, "Deep Vein Thrombosis ("DVT") And Thermal/Compression Therapy Systems, Apparatuses And Methods", filed Mar. 13, 2012, the entire contents of each of which are incorporated herein by reference.

BACKGROUND

The present disclosure relates generally to orthopedics and in particular to the therapeutic cooling of a sore or injured body part.

It is known to use chilled water to cool and sooth a sore or injured body part. For example, U.S. Pat. Nos. 5,241,951 and 5,330,519 describe a cold therapy unit that uses chilled water. The patents call for a variable flow restrictor for temperature control. The more the flow restrictor is restricted, the less water flows through the cooling pad, resulting in a higher therapy pad temperature. The less the flow restrictor is restricted, the more water flows through the cooling pad, resulting in a lower therapy pad temperature.

While known devices have provided therapeutic cooling, the devices have had certain drawbacks. For instance, temperature control for certain of these devices has been difficult, leading to instances in which water has been chilled to a level that is uncomfortable for the patient. Also, certain devices cause the ice to melt too quickly, expending the thermal potential of the device. Further, certain devices have difficulty maintaining an even temperature distribution across their therapy pads.

An improved cold therapy system is needed accordingly.

SUMMARY

The present disclosure sets forth multiple primary embodiments, each of which uses a heat exchanging therapy pad that maintains a very even temperature profile over the entire therapy pad. The heat exchanging therapy pad is made from three layers sealed or welded together in one embodiment. There is an outer layer and in inner layer, which are both thick relative to a middle layer located between the outer and inner layers. For example, the outer and inner layers can be fifteen mils (0.015 inch or 0.38 millimeter (mm)) thick, while the middle layer can be five mils (0.005 inch or 0.13 mm thick). The thinness of the middle layer makes that layer a good heat exchanger even though the middle layer is non-metallic in one embodiment. The layers can each be any combination of urethane, polyurethane, or vinyl for example. The outside surface of the outer layer is provided with a hook or pile material, which receives a mating pile or hook strap for securing the heat exchanging therapy pad to a patient, e.g., to the patient's knee or shoulder. The inside of the inner layer is provided with a soft satin finish in one embodiment for comfortable contact with the patient.

The three layers are sealed, e.g., radio frequency ("RF") welded, along the entire perimeter of the shape or profile of the therapy pad. The three layers can be sealed, e.g., welded together simultaneously. The three layers are also sealed or welded so as to have inner flowpath-forming seams, which can be continuous or intermittent. The flow path-forming seams are provided in each of an upper, non-patient contacting, chilled-water chamber and a lower, patient-contacting chamber. The chilled-water chamber is formed via the upper and middle layers, while the patient-contacting chamber is formed by the middle and lower layers. The flowpath through the chilled-water chamber is in one embodiment the same as and resides on top of the flowpath through patient-contacting chamber. The discharge end of the flowpath through the chilled-water chamber, however, becomes the entrance end of the flowpath through patient-contacting chamber. In this manner, the heat exchanger is a countercurrent heat exchanger, with the warmest water about to leave the therapy pad to return to a cooling bath meeting the coldest chilled water just entering the therapy pad.

The three layers are further sealed or welded so as to accept a liquid inlet (e.g., tube) and a liquid outlet (e.g., tube). The liquid inlet tube is sealed into the chilled-water chamber, while the liquid outlet tube is sealed into the patient-contacting chamber. The tube ends residing within the chambers are angled in one embodiment to prevent the ends from being occluded if the pad is bent or folded during use, e.g., when applied to the patient's knee, shoulder or other appendage.

The tubes each reside on a same side of an entrance/exit seam that extends into the therapy pad adjacent the inlet and outlet tubes. Such arrangement allows the chilled water entering the upper chilled-water chamber to be directed towards oncoming warmed water flowing towards the entrance/exit seam in the lower patient-contacting chamber. A hole or aperture is formed in the middle layer on the opposing side of the entrance/exit seam from the inlet and outlet tubes. The hole or aperture is formed in the middle layer and allows the water at the end of the chilled-water chamber flowpath to flow into the beginning of the patient-contacting chamber flowpath. The hole or aperture is located roughly midway along the cross-section of the flowpath, so that the hole or aperture is difficult to occlude. To occlude the hole, one of the upper or lower layers would have to be pressed against water or fluid pressure into the hole or aperture, which is difficult and unlikely, especially for a sustained amount of time.

Pinch spots are also formed, e.g., RF welded, into the inner portion of the heat exchanging therapy pad. The pinch or weld spots help to relieve stress on the peripheral seals or welds and also turbulate fluid flow within the pad. The spacing between the pinch or weld spots affects the flowrate of water through the pad. In one embodiment, the spacing is set so the at average distance between each adjacent pinch or weld spot is at least ½ inch (12.7 mm) and in one embodiment ⅝ inch (15.9 mm).

A stretchable wrap or strap is used to secure the heat exchanging therapy pad to the patient in one embodiment. The wrap or strap can be completely separate from the pad and have dimensions for example of four inches (10.2 centimeters ("cm")) wide by twenty-four inches (61 cm) long in one implementation. One end of the wrap or strap is provided with a first hook or pile strip that attaches releasably to the pile or hook outer surface of the heat exchanging therapy pad. The majority of the wrap or strap includes the other of a pile or hook material, different than the material of the strip. The opposing end of the wrap or strap includes a second hook or pile strip having the same material as the first strip. The second hook or pile strip secures releasably to the pile or hook material, respectively, located on the outside of the middle part of the wrap or strap. The wrap or strap thus secures at its second end to itself, wrapping tightly and releasably around the heat exchanging therapy pad.

The heat exchanging therapy pad receives chilled water from and returns warmed water to a cooling bath. The patient-contacting chamber of the heat exchanging therapy pad receives heat from the patient and delivers heat to the chilled-water chamber of the heat exchanging therapy pad. The volume of fluid within the overall pad is relatively large compared to the flowrate of water through the pad. This allows the pad's patient contacting surface temperature to be very even across the entire surface.

In a first primary cold therapy system embodiment, a fixed fluid restrictor can be placed in the warmed water return line extending from the heat exchanging therapy pad to the cooling bath. The fixed fluid restrictor is optimized to provide a desired fluid temperature in the therapy pad, e.g., 45° F. (7.2° C.), assuming an average fluid temperature in the cooling bath of, e.g., 32° F. (0° C.) to 34° F. (1.1° C.), an average heat transfer from the patient and a pump flowrate of about 250 milliliters ("ml") per minute. In this first primary embodiment, the user does not adjust a valve or other control to adjust the temperature. The user can however vary the amount of ice or other cooling mechanism that is placed in the cooling bath, e.g., a frozen gel pack or multiple ones of same. A readout, e.g., a digital light-emitting diode ("LED") or liquid crystal display ("LCD") readout is provided to inform the user of the temperature of the fluid flowing into the heat exchanging therapy pad in one embodiment.

In a second primary cold therapy system embodiment, the flow restrictor is variable. The flow restrictor can be manually variable, e.g., via a rotatable knob, dial or lever, or via a translating lever. The manual actuation opens or closes a cam, plunger or clamp to in turn open or close a tube of the cold therapy system, such as the tube returning from the heat exchanging therapy pad to the cooling bath. The restrictor can alternatively be actuated automatically via a motor in response to the patient's input of a desired temperature or other setting and a microprocessor conversion of the patient input to a motor command to move the restrictor plunger or cam to the set position. In either embodiment, the fixed restrictor or the variable restrictor is placed at the cooling bath end of the tube returning form the heat exchanging therapy pad to the cooling bath, such that the tube and the therapy pad are both pressurized and inflated.

Opening the cold therapy unit line, e.g., the return line, allows the flowrate to increase, bringing more chilled water to the heat exchanging therapy pad per unit volume of the pad and thus lowering the patient-contacting surface of the pad and the patient's skin temperature. Closing the cold therapy unit line, e.g., the return line, forces the flowrate to decrease, bringing less chilled water to the heat exchanging therapy pad per unit volume of the pad and thus raising the patient-contacting surface of the pad and the patient's skin temperature. Even though different patients bring different thermal loads to the overall thermodynamic system created by the heat exchanging therapy pad, the adjustable restrictor nevertheless enables treatment temperatures for most all patients to be maintained between 41° F. (5° C.) to 48° F. (8.9° C.).

The '022 Application incorporated by reference above describes a thermal compression therapy in which a cooling pad, such as the heat exchanging therapy pad of the present disclosure, is wrapped by an air bladder. The air bladder is then inflated by pressurized air. The air in the bladder is pressurized generally to around one psig. The pressure of water within the heat exchanging therapy pad is in one embodiment around nine psig. Thus the heat exchanging therapy pad when inflated during use can readily withstand the lower pressure applied by an outer-wrapped air bladder. It is therefore expressly contemplated to use the heat exchanging therapy pad of the present disclosure in a combination therapy with an outer air bladder, including with any combination treatments illustrated and described in the '022 Application.

It is accordingly an advantage of the present disclosure to provide a cold therapy unit with improved therapy pad temperature control.

It is another advantage of the present disclosure to provide a cold therapy unit that cools the user safely.

It is a further advantage of the present disclosure to provide a cold therapy unit that efficiently and effectively incorporates a heat exchanger that exchanges heat from fluid warmed by the patient.

It is yet another advantage of the present disclosure to provide a cold therapy unit that combines a heat exchanger with a therapy pad, yielding an overall simple and effective fluidic cooling system.

It is yet a further advantage of the present disclosure to provide a cold therapy unit having a therapy pad that maintains at least a substantially uniform temperature across the patient-contacting surface.

Additional features and advantages are described herein, and will be apparent from the following Detailed Description and the figures.

BRIEF DESCRIPTION OF THE FIGURES

FIG. 3 is a plan view of one embodiment of a heat exchanging therapy pad of the present disclosure, which may be used with the systems of either FIG. 1 or 2.

FIG. 4 is a sectioned elevation view taken along line IV-IV in FIG. 3.

DETAILED DESCRIPTION

Fixed Flowrate System

Figure 1:
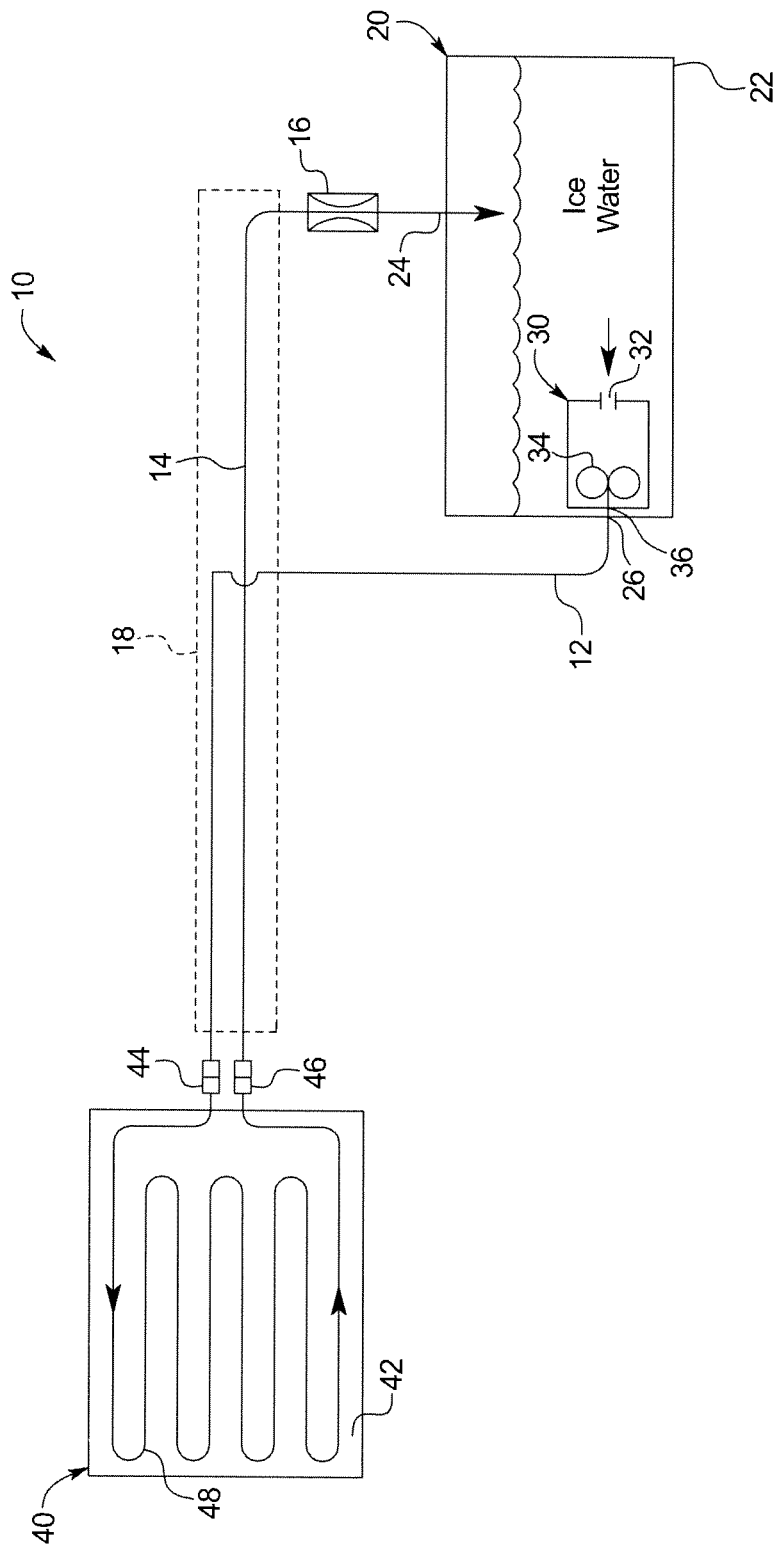
FIG. 1 is a schematic view of one embodiment of a cold therapy system of the present disclosure.

Referring now to the drawings and in particular to FIG. 1, one embodiment of a cold therapy system of the present disclosure is illustrated by system 10. Primary components of system 10 include tubing or lines 12 and 14, a cooling bath 20 and a heat exchanging therapy pad 40. Each of these items is discussed in detail below. As illustrated, there are a number of lines or passageways that link cooling bath 20 to heat exchanging therapy pad 40. For instance, a to-pad line 12 extends from a bath outlet 26 of cooling bath 20 to a liquid inlet 44 of heat exchanging therapy pad 40. A from-pad line 14 extends from liquid outlet 46 of heat exchanging therapy pad 40 to return inlet 24 of cooling bath 20.

In an embodiment, each of lines 12 and 14 is a tube, such as a ¼ inch (6.4 millimeters ("mm")), 5/16 inch (7.9 mm), or ⅜ inch (9.5 mm) outer diameter tube, which can be made of polyvinyl chloride ("PVC"), urethane, or polyurethane, for example. The tubing for lines 12 and 14 can have a wall thickness of 0.031 inch (0.79 mm), 0.063 inch (1.6 mm), or larger. The tubing for lines 12 and 14 is flexible in one embodiment for bending.

As illustrated in FIG. 3, shorter tube segments corresponding to lines 12 and 14 extend into the heat exchanging therapy pad (and possibly out of for sealed connection to lines 12 and 14). The tube segments can be of the same diameter as that of the tubes for lines 12 and 14, or have smaller diameters and wall thicknesses. The pad tube segments may be of a more rigid material, such as polyurethane or rigid PVC, but in any event are compatible with the material of therapy pad layers with respect to whatever type of sealing process is used, e.g., radio frequency ("RF") welding.

In an embodiment, tubing or lines 12 and 14 are run together as much as possible and are housed within a thermally insulating sleeve or jacket 18, such as an extruded polyurethane foam sleeve. Sleeve 18 enables the user or patient to easily and collectively maneuver lines 14 and 16 and place heat exchanging therapy pad 40 at a desired location on the patient's body. Sleeve 18 may be broken or separated in one or more places, e.g., via quick-disconnect fittings. The breaks between the ends of to-pad line 12 and from-pad line 14 allow lines 12 and 14 and sleeve 18 to be transported in smaller segments, and/or allow for an intervening display unit and/or control unit to be spliced into lines 12 and 14 and sleeve 18 at desired locations.

Cooling bath 20 includes a housing 22 that is made of a thermally insulating plastic. Housing 22 can have an inner shell made for example from a dishwasher safe polypropylene plastic, and an outer shell and a lid both made for example from medium density polyethylene. Housing 22 in an embodiment includes a hinged or otherwise removable lid, which allows access to the inside of housing 22 and cooling bath 20. The inner and outer shells separate an insulating area that can either be evacuated or filled with an insulating material, such as insulating foam, e.g., polyurethane insulation foamed in place or a sheet of insulation such as Thinsulate™. Further alternatively, air between the inner and outer shells serves as an insulator.

A liquid pump 30 is placed within bath housing 22 of cooling bath 20 and in an embodiment is allowed to (i) rest on the bottom of bath housing 22, (ii) be removeably secured to the bottom or lower portion of one of the side walls of bath housing 22 or (iii) be removeably secured to the lid of cooling bath 20. In any case, liquid pump 30 is configured to be submerged beneath a volume of ice water that is filled within bath housing 22. Liquid pump 30 includes a pump inlet 32, a pump motor 34 and a pump outlet 36. In the illustrated embodiment, pump outlet 36 communicates fluidly with to-pad line 12 running to heat exchanging therapy pad 40.

Figure 2:
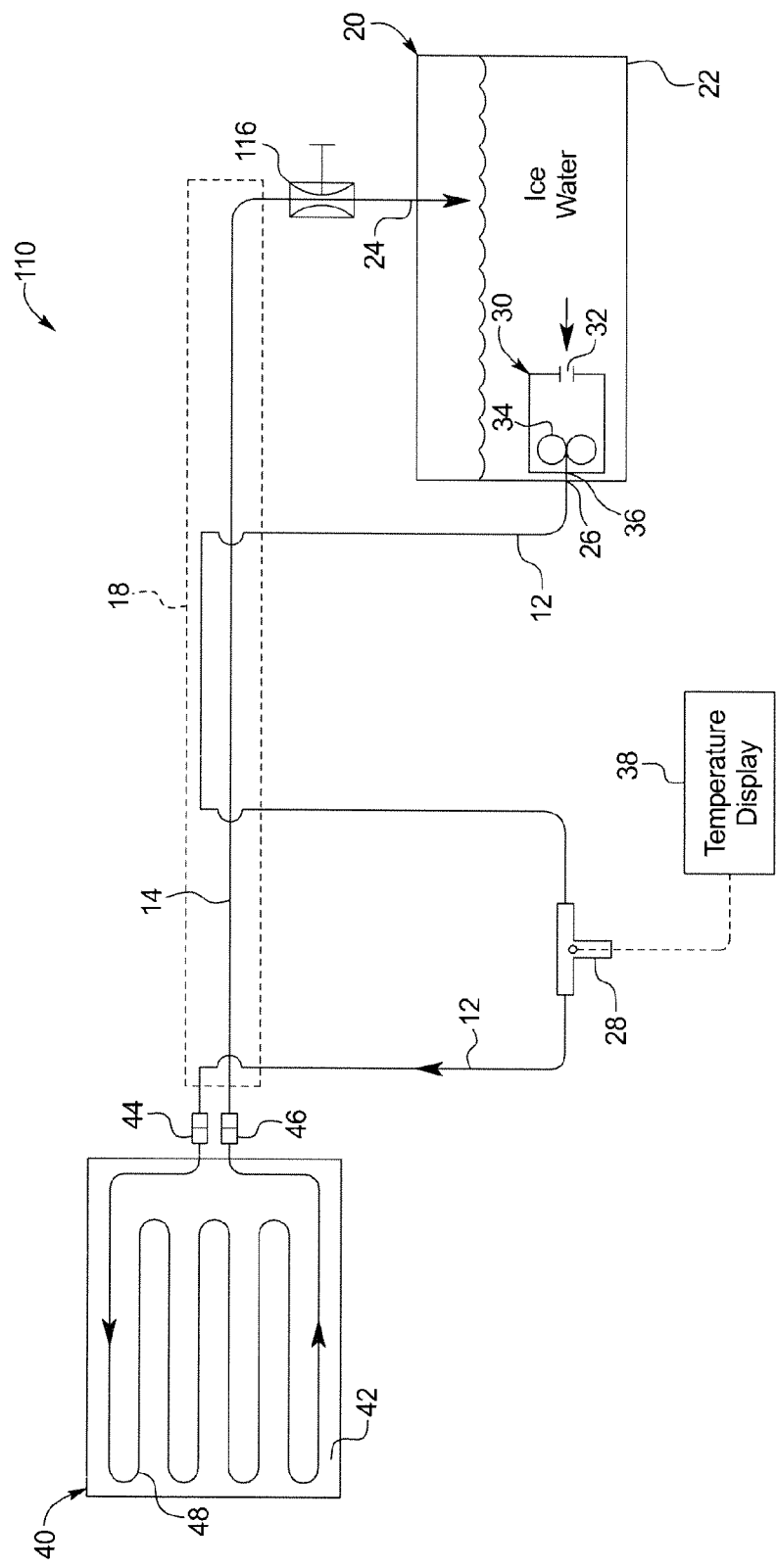
FIG. 2 is a schematic view of a second embodiment of the cold therapy system of the present disclosure.

In system 10 of FIG. 1, the flowrate may be fixed such that pump motor 34 outputs water pulled in from inlet 32 through outlet 36 at a pressure of about 9.0 psig and a flowrate of 250 ml per minute. So as not to stress the pump, it is contemplated to use a pump that is physically be able to pump water up to 1500 ml per minute at about 4.5 psig. FIG. 2 illustrates an alternative cold therapy system in which the flowrate may be varied. The flowrate in FIG. 2 may be varied over a range of, for example, 120 ml per minute to 375 ml per minute, within which the pressure does not stray too far away from 9 psig, so that heat exchanging therapy pad 40 remains properly inflated.

In an embodiment, pump motor 34 is powered via house voltage, such as 140 VAC or 440 VAC, or is alternatively fed via a power supply, such as a direct current ("DC") power supply. Pump motor 34 includes a hermetically sealed power connection. A water-proof power cord is run in one embodiment from pump motor 34 to an electrical port (not illustrated) located on the outside of bath housing 22. Alternatively, the cord is run through insulating sleeve 18 holding pathways 12 and 14, to a location at which a power cord electrical port (not illustrated) is provided, e.g., at a control unit spliced into lines 12 and 14 and sleeve 18 as mentioned above.

In the embodiment illustrated in FIG. 1, a fixed restrictor 16 is placed in from-pad line 14 just upstream of bath return inlet 24 of cooling bath 20. Fixed restrictor 16 can be a reduced diameter union or section of tubing that creates a back-pressure in from-pad line 16 and heat exchanging therapy pad 40, so as to help inflate and maintain pressure the therapy pad. In an alternative embodiment, fixed restrictor 16 is placed in from-pad line 16 just downstream of pad outlet connector 46 or elsewhere along the middle of from-pad line 14.

Liquid pump 30 pumps ice water from bath housing 22 through to-pad line 12 into a chilled-water chamber of heat exchanging therapy pad 40. The chilled water accumulates heat from a patient-contacting chamber of heat exchanging therapy pad 40, which in turn accumulates heat from the patient. The water exits the patient-contacting chamber of heat exchanging therapy pad 40 and returns to cooling bath 20. The cycle just described is run continuously and for as long as the user desires and/or as long as there is a temperature gradient between heat exchanging therapy pad 40 and cooling bath 20.

In the embodiment of system 10, the patient is provided with no ability to make temperature adjustments other than to vary an amount of ice and/or water placed in bath housing 22 of cooling bath 20 and to adjust the position of heat exchanging therapy pad 40. Fixed restrictor 16 is again fixed and thus does not provide a user with the ability to vary therapy fluid temperature.

Variable Flowrate System

Referring now to FIG. 2, system 110 is illustrated and does provide the user with the ability to vary the flowrate and thus the temperature of the fluid flowing through heat exchanging therapy pad 40. System 110 also adds a temperature sensor 28 and a temperature display 38, which can also be provided with system 10 of FIG. 1 if desired. Temperature sensor 28 can be a thermistor or thermocouple, which outputs a voltage to a light-emitting diode ("LED") display or liquid crystal display ("LCD"). Temperature sensor 28 in one embodiment measures the temperature of the water just before entering heat exchanging therapy pad 40. As discussed above, the hermetically sealed power wires from liquid pump 30 run in one embodiment through the insulating sleeve surrounding pathways 12 and 14. It is contemplated to terminate the power wires and the wires of sensor 28 at a patient control station located within sleeve 18, which houses temperature display 38. Alternatively, temperature sensor 28 is located within the control station. Further alternatively, temperature sensor 28 is located near heat exchanging therapy pad 40 but has signal wires that run to cooling bath 20 where temperature display 38 is located.

The primary difference between system 110 of FIG. 2 and system 10 of FIG. 1 is the provision of a manually adjustable restrictor 116 that replaces fixed restrictor 16 in FIG. 1. Adjustable restrictor 116 can be placed anywhere in system 110 discussed above for restrictor 16 and system 10, such as at the bath end of from-pad line 14, at the therapy pad end of from-pad line 14, or any where desirable in return line 14 between bath 20 and heat exchanging therapy pad 40.

Adjustable restrictor 116 in an embodiment includes a cam that can be turned to restrict from-pad tube 14 from being fully open continuously decreasing to being ¼ closed, ½ closed, ¾ closed, fully closed or at whatever low flow limit is desired. While adjustable restrictor 116 is adjusted in one embodiment manually by a knob, dial, lever, sliding device or other adjuster, adjustable restrictor 116 is alternatively controlled by a motor, e.g., via a small ball screw, to adjust the cam or variable clamp by an amount inputted by the user into a control pad, e.g., digitally via a keypad. A microprocessor then converts the inputted amount into a motor control signal for automatically setting the cam or variable clamp.

For a given thermal patient load, opening from-pad line 14 via adjustable restrictor 116 causes the flowrate to increase, thereby causing the heat exchanging therapy pad 40 temperature that the patient sees to drop. For a given thermal patient load, closing from-pad line 14 via adjustable restrictor 116 causes the flowrate to decrease, thereby causing the heat exchanging therapy pad 40 temperature that the patient sees to increase. The patient's physiology does affect the output of systems 10 and 110. A large adult male may be cooled to 52° F. (11° C.), while the same flowrate setting may cool a frail child or elderly person to 41° F. (5° C.). Adjustable restrictor 116 enables the flowrate to be adjusted so that the patient's body temperature achieves an effective but safe therapeutic temperature, e.g., 45° F. (7.2° C.).

Housing and Pump Mounting

FIGS. 7 to 10 of the '476 Application cross-referenced above teach one embodiment for a bath housing and its integration of the liquid pump and a heat exchanger. In the present application, the heat exchanger is incorporated instead into heat exchanging therapy pad 40 and is thus not provided inside bath housing 22 of the present application. However, the configuration of the bath housing of the '476 Application and the mounting of its pump are applicable and thereby incorporated into the present disclosure for both systems 10 and 110.

In particular, FIG. 7 of the '476 Application illustrates that its housing can have a completely removable lid. The lid is alternatively hinged. The base of its housing can include a rotating handle for transport of the unit. As further illustrated in FIG. 7 of the '476 Application, the lid holds the pump such that the pump extends vertically downward into the liquid/ice within the bath. The inlet of the pump is at the bottom of the pump in one embodiment, such that when the pump is positioned operably within the base of the housing, the pump inlet is located advantageously near the bottom of the housing. Locating the pump inlet near the bottom of the housing helps the cold therapy system to operate even when the user does not fill the liquid/ice to the suggested level. The location also helps the pump, lines 12 and 14, and heat exchanging therapy pad 40 to prime and run smoothly when the user does fill the liquid/ice to the suggested level. The above designated structure is desirable for implementing bath 20 and pump 30 in the present disclosure and is accordingly incorporated herein by reference.

Heat Exchanging Therapy Pad

Referring now to FIGS. 3 and 4, both systems 10 and 110 employ heat exchanging therapy pad 40. Heat exchanging therapy pad 40 includes a flexible, wrapable body 42. Wrapable body 42 in the illustrated embodiment is made from three layers 48, 50 and 52 sealed or welded together in one embodiment. There is an outer layer 48 and in inner layer 52, which are both thick relative to a middle layer 50 located between the outer and inner layers. For example, outer and inner layers 48 and 52 can be greater than or equal to twelve mils (0.012 inch or 0.30 millimeter ("mm")) thick, e.g., fifteen mils (0.015 inch or 0.38 mm) thick. Middle layer 50 can be less than or equal to seven mils (0.007 inch or 0.18 mm) thick, e.g., five mils (0.005 inch or 0.13 mm) thick. The thickness of outer layer 48 and inner layer 52 makes the layers more insulative. The thinness of the middle layer 50, on the other hand, makes the layer a good heat exchanger even though the middle layer is non-metallic in one embodiment.

Layers 48, 50 and 52 can be made of any combination of urethane, polyurethane, or vinyl for example. The outside surface of outer layer 48 is provided with a hook or pile material, which receives a mating pile or hook stretchable wrap or strap (not illustrated) for securing the heat exchanging therapy pad to a patient, e.g., to the patient's knee or shoulder. The wrap or strap can be completely separate from the pad and be, for example, twenty-four inches (61.0 centimeters ("cm")) long by four inches (10.2 cm) wide in one implementation. One end of the wrap or strap is provided with a first hook or pile strip that attaches releasably to the pile or hook of the outer surface of outer layer 48. The majority of the wrap or strap includes the other of a pile or hook material, which is different than that of the strip. The opposing end of the wrap or strap includes a second hook or pile strip, which is of the same material as the first strip. The second hook or pile strip secures releasably to the pile or hook material, respectively, of the majority or middle part of the wrap or strap. The wrap or strap thus secures at its second end to itself, wrapping tightly and releasably around heat exchanging therapy pad 40.

The inside surface of inner layer 52 is provided with a soft satin finish in one embodiment for comfortable contact with the patient. The three layers 48, 50 and 52 are sealed, e.g., radio frequency ("RF") welded, along the entire perimeter P of the shape or profile of the therapy pad. The three layers can be sealed, e.g., welded together simultaneously. Alternatively, three layers 48, 50 and 52 can be ultrasonically welded, heat sealed and/or solvent bonded together and/or to form any of internal structures discussed herein. For ease of discussion, hereafter, the layers will be referred to as sealed or welded together.

Layers 48, 50 and 52 are also sealed or welded so as to have inner flowpath-forming seams 54a to 54f, which can form an overall continuous or intermittent seam. In the illustrated embodiment, flowpath-forming seams 54a to 54f are intermittent overall and leave gaps G. Gaps G are provided primarily so that wrapable body 42 can more easily bend and flex about the patient's body part, e.g., knee, shoulder or other appendage. It is not expected that much water will travel through gaps G. As illustrated, perimeter P of wrapable body 42 can take sharp turns, creating ears or flaps, which help pad 40 to wrap around and cover an oddly shaped body part.

The flowpath forming seams 54a to 54f are provided in each of an upper, non-patient contacting, chilled-water chamber 60 (FIG. 4) and a lower, patient-contacting chamber (FIG. 4). Chilled-water chamber 60 is formed via upper and middle layers 48 and 50, while the patient-contacting chamber is formed by the middle and lower layers 50 and 52. Thus a flowpath (as shown by dotted line 58) through the chilled-water chamber 60 is the same (but in the opposite direction) as, and resides on top of, the flowpath through patient-contacting chamber 62. The discharge end of flowpath 58 through the chilled-water chamber 60, however, becomes the entrance end of the flowpath through patient-contacting chamber 62. In this manner, heat exchanger pad 40 forms a countercurrent heat exchanger, with the wannest water about to leave therapy pad 40 (at outlet tube 46) to return to cooling bath 20 meeting (via thin layer 50) the coldest chilled water just entering the therapy pad 40 (via inlet tube 44).

Layers 48, 50 and 52 are further sealed or welded so as to accept a liquid inlet (e.g., tube 44) and a liquid outlet (e.g., tube 46). Tubes 44 and 46 may be ports, e.g. barbed ports, onto which lines 12 and 14 are respectively press-fitted. Tubes 44 and 46 may alternatively be longer pigtails that extend within a section of insulating sleeve 18. That section of insulating sleeve 18 then connects to a section of sleeve 18 extending from bath 20 holding lines 12 and 14. The tubes 44 and 46 and lines 12 and 14 within sections of sleeve 18 may connect removeably and respectively to each other, e.g., via quick-disconnect fittings.

Liquid inlet tube 44 is sealed into chilled-water chamber 60, while liquid outlet tube 46 is sealed into the patient-contacting chamber 62. That is, liquid inlet tube 44 is sealed to and between layers 48 and 50, while liquid outlet tube 46 is sealed to and between layers 50 and 52. Tube ends 44a and 46a residing within chambers 60 and 62, respectively, are angled in the illustrated embodiment to prevent tubes ends 44a and 46a from being occluded if the pad body 42 is bent or folded during use, e.g., when applied to the patient's knee, shoulder, or other appendage.

Tubes 44 and 46 each reside on a same side of an entrance/exit seam 54a that extends into therapy pad body 42 adjacent the inlet and outlet tubes. Such arrangement allows the chilled water entering the chilled-water chamber 60 to be directed towards (upwards in FIG. 3) oncoming wanted water flowing towards the entrance/exit seam 54a in the patient-contacting chamber 62. A hole or aperture 64 is formed in middle layer 50 on the opposing side of the entrance/exit seam 54a from tubes 44 and 46. Hole or aperture 64 in middle layer 50 allows the water at the end of flowpath 58 in chilled-water chamber 60 to flow into the beginning of the corresponding flowpath of patient-contacting chamber 62, continuing countercurrent to and beneath flowpath 58, and exiting outlet tube 46. Hole or aperture 64 is located roughly midway along the cross-section of flowpath 58 so that the hole or aperture is difficult to occlude against the pressurized water in pad body 42. Hole or aperture 64 may alternatively be a series of holes or apertures and/or be non-circular, such as oblong.

Pinch spots or baffles 66 are also formed, e.g., RF welded, into the inner portion of the heat exchanging therapy pad body 42. Pinch or weld spots 66 help to relieve stress on the seals of periphery P and also turbulate fluid flow along the chilled water flowpath 58 and the patient flowpath. The spacing between pinch or weld spots 66 affects the flowrate of water through pad body 42. In one embodiment, the spacing is set so the at average distance between each adjacent pinch or weld spot 66 is at least ½ inch (12.7 mm) and in one embodiment ⅝ inch (15.9 mm).

Heat exchanging therapy pad 40 receives chilled water from and returns warmed water to cooling bath 20. Patient-contacting chamber 62 receives heat from the patient and delivers heat to the chilled-water chamber 60 of the heat exchanging therapy pad. The volume of fluid within the overall pad body 42 is relatively large compared to the flowrate of water through the pad. In one embodiment the total volume of pad body 42 is 550 ml. An average flowrate through pad 40 of 250 ml/min will thus flow 250 ml through the pad over one minute. This leaves a ratio of pad volume to a one minute flow volume of about 2.2:1. For the thicknesses of layers 48, 50 and 52, pad 40 can be sized and/or the liquid flowrate can be set so that the ratio of pad volume to a one minute flow volume is anywhere at or between about 1:1 to 2.5:1. Different material thicknesses and/or different overall pad volumes may call for a different range of ratios. In any case, maintaining the ratio at or within the range causes the temperature of the pad's patient contacting surface (inner surface of inner layer 52) to be very even across its entire surface. To operate within the ratio range, it is contemplated for system 10 to provide smaller pads with lines 12 and 14 having an extra or more restrictive fixed restrictor 16. Variable restrictor 116 of system 110 is configured to be able to occlude return line 14 enough to accommodate even the smallest pads for use with the system.

The pressure inside both chilled-water chamber 60 and patient-contacting chamber 62 can be from about five psig to about twelve psig, e.g., about nine psig. Such pressure allows for an external pressurized air wrap to be placed around pad 40. The air wraps are typically pressurized to about one psig to provide compression therapy to the patient in addition to the cold therapy provided by pad 40 (sometimes called a combination therapy). The one psig air pressure does not affect the inflation of pad body, which is pressurized as discussed to at least five psig. It is therefore expressly contemplated to use heat exchanging therapy pad 40 in any of the combination therapies discussed above in the incorporated '022 Application.

Lines 12 and 14 are fed into pad body 42 along the right side illustrated in FIG. 3. Pad body 42 is typically donned such that lines 12 and 14 approach pad body 42 from underneath the body. This configuration and application of pad body 42 enables lines 12 and 14 to extend downwardly due to gravity and out to cooling bath 20 without kinking.

Operation

Testing of heat exchanging therapy pad 40 has been performed. For testing, and consistent with the above description, the pad featured three layers with an outer layer of fifteen mils (0.015 inch or 0.38 millimeter (mm)) polyurethane (which had a pile surface to engage hook fasteners). The inner layer that contacted the skin was also fifteen mils (0.015 inch or 0.38 millimeter (mm)) thick and was made of a clear urethane material having a soft satin finish. A five mils (0.005 inch or 0.13 mm thick) to seven mils (0.007 inch or 0.18 mm) thick clear layer of urethane material was placed between the inner and outer layers to create a heat exchange membrane.

Consistent with FIG. 3, the tested water inlet tube from the pump entered the pad between the middle thin membrane layer and the top layer with the pile surface. The water made a complete circuit through the serpentine labyrinth in the outer chamber and then funneled through a hole in the middle or center urethane layer and entered the patient chamber closest to the skin. The water then continued back along the same path in the lower chamber below the upper chamber, exiting via the outlet tube. The water entered the top chamber at 33° F. to 34° F. (0.6° C. to 1.1° C.), but quickly exchanged heat with the exiting water in the lower chamber, which produced the water's warmest temperature.

Objectives of the study were to (i) verify that the three layer heat exchanger pad was capable of providing a safe even water temperature to a bodypart, e.g., the leg, above 40° F. (4.4° C.) and (ii) to document the temperature variance across the entire pad surface. It was hypothesized that with the appropriate flow, the three layer pad would produce safe temperatures in excess of 40° F. (4.4° C.) plus a margin of safety. The following materials were used in the testing: (i) a YSI thermocouple probe and gauge; (ii) the three layer heat exchange pad described above; (iii) a Cooling Unit A; and (iv) a Cooling Unit B.

In a first test, the three layer pad was connected to Cooling Unit A with an outlet tube to the pad and a return tube back to the reservoir. The pad was placed on an insulated polyethylene foam surface on a desktop to insulate the pad from the desk. The YSI thermocouple probe was first calibrated against a lab thermometer in freezing water and then placed on the inside bare pad surface immediately above the hole in the middle layer where the water transitions from the outer chamber to the lower chamber. A small foam piece was placed over the thermocouple, while three ceramic squares each with a cork base and an aluminum weighted top were stacked to balance over the thermocouple probe to maintain the probe in contact with the pad surface.

Ambient air was used as the heat source on the exposed pad surface, which has been found from past experience to be a good approximation (within a couple of degrees) of a cold soaked leg. The thermocouple was moved, starting from being directly above the holes in the middle layer to many different points on the inside base pad layer. The temperature was allowed to equilibrate until the reading remained the same for five minutes. That reading was recorded. The results showed that all temperature readings were between 7.5° C. and 8° C. (45.5° F. and 46.4° F.) and thus were (i) well within the desired safe and effective therapeutic range and (ii) very consistent across the entire inner pad surface.

A second test was repeated using the setup of the first test but instead using Cooling Unit B, which flowed 32° F. (0° C.) degree water to the pad. The same procedure was used to calibrate the equipment, take the readings, equilibrate the temperatures and record the results. Each position for Cooling Unit B resulted in the same 7° C. (43° F.). temperature reading across each region of the pad. Again, the temperature readings were (i) well within the safe zone and (ii) very consistent.

The final test positioned the pad in place on a subject's leg. The thermocouple probe was placed between the pad and the subject's leg in several positions and allowed to equilibrate after the pad was left on the leg for thirty minutes. The results for all positions tested showed a range of temperature from 11° C. to 11.5° C. (51.8° F. to 52.7° F.). As discussed above, the flow rate through the pad would need to be increased in this scenario to drop the therapy temperature into a desired lower range, but importantly, the temperatures were quite even across the entire pad surface.

Additional Aspects of the Present Disclosure

Aspects of the subject matter described herein may be useful alone or in combination one or more other aspect described herein. Without limiting the foregoing description, in a first aspect of the present disclosure, which can be used in combination with any other aspect listed herein, a cold therapy system includes: a cooling bath structured to chill and hold chilled water; a pump positioned and arranged to pump the chilled water; a to-pad line positioned and arranged to hold chilled water pumped by the pump from the cooling bath; a from-pad line positioned and arranged to hold water returning to the cooling bath; and a therapy pad in fluid communication with the to- and from-pad lines, the therapy pad including a patient-contacting chamber that is in heat exchange communication with a chilled-water chamber residing outside of the patient-contacting chamber when the therapy pad is donned.

In a second aspect of the present disclosure, which can be used in combination with any other aspect listed herein, the pump is located inside the cooling bath.

In a third aspect of the present disclosure, which may be used in combination with any other aspect listed herein, the to-pad line and the from-pad line are run together from the cooling bath to the therapy pad.

In a fourth aspect of the present disclosure, which may be used in combination with any other aspect listed herein, the cold therapy system includes a flow restrictor placed in the from-pad line.

In a fifth aspect of the present disclosure, which may be used with the fourth aspect in combination with any other aspect listed herein, the flow restrictor is variable.

In a sixth aspect of the present disclosure, which may be used with the fifth aspect in combination with any other aspect listed herein, the flow restrictor is manually variable.

In a seventh aspect of the present disclosure, which may be used with the fourth aspect in combination with any other aspect listed herein, the flow restrictor is positioned at the cooling bath end of the from-pad line.

In an eighth aspect of the present disclosure, which may be used in combination with any other aspect listed herein, the to-pad line is placed in fluid communication with the chilled water chamber and the from-pad line is placed in fluid communication with the patient-contacting chamber.

In a ninth aspect of the present disclosure, which may be used in combination with any other aspect listed herein, a cold therapy system includes: a cooling bath structured to chill and hold chilled water; a pump positioned and arranged to pump the chilled water; a to-pad line positioned and arranged to hold chilled water prepared by the pump from the cooling bath; a from-pad line positioned and arranged to hold water returning to the cooling bath; and a therapy pad in fluid communication with the to- and from-therapy lines, the therapy pad including a patient-contacting chamber that is in heat exchange communication with a chilled-water chamber, the volume of the therapy pad when inflated having a ratio to a volume of liquid that is pumped by the pump through the therapy pad over one minute of at least 1:1.

In a tenth aspect of the present disclosure, which may be used with the ninth aspect in combination with any other aspect listed herein, the volume of the therapy pad when inflated compared to the volume of the liquid that is pumped by the pump through the therapy pad over one minute is within a range of 1:1 to 2.5:1.

In an eleventh aspect of the present disclosure, which may be used with any other aspect listed herein, the heat exchange communication is a countercurrent heat exchange communication.

In a twelfth aspect of the present disclosure, which may be used with any other aspect listed herein, a therapy pad for a cold therapy system includes: an outer layer; an inner layer; a middle heat exchange layer; a liquid inlet; and a liquid outlet, wherein the layers are sealed together such that the outer layer and the middle heat exchange layer form a chilled-water chamber, the inner layer and the middle heat exchange layer form a patient-contacting chamber, the liquid inlet is in sealed communication with the chilled-water chamber, and the liquid outlet is in sealed communication with the patient-contacting chamber.

In a thirteenth aspect of the present disclosure, which may be used with the twelfth aspect in combination with any other aspect listed herein, the middle heat exchange layer is at least half as thin as at least one of the inner or outer layers.

In a fourteenth aspect of the present disclosure, which may be used with the twelfth aspect in combination with any other aspect listed herein, the middle heat exchange layer is equal to or less than 0.007 inch (0.18 mm) thick.

In a fifteenth aspect of the present disclosure, which may be used with the twelfth aspect in combination with any other aspect listed herein, the layers are further sealed together so as to form a first serpentine flowpath in the chilled-water chamber and a second serpentine flowpath in the patient-contacting chamber.

In a sixteenth aspect of the present disclosure, which may be used with the fifteenth aspect in combination with any other aspect listed herein, the first serpentine flowpath matches, at least substantially, the second serpentine flowpath.

In a seventeenth aspect of the present disclosure, which may be used with the fifteenth aspect in combination with any other aspect listed herein, the middle heat exchange layer forms an aperture that enables an outlet end of the first serpentine flowpath to communicate with an inlet end of the second serpentine flowpath.

In an eighteenth aspect of the present disclosure, which may be used with the twelfth aspect in combination with any other aspect listed herein, the liquid inlet includes a first tube sealed to a chilled-water side of the middle heat exchange layer and the liquid outlet includes a second tube sealed to a patient-contacting side of the middle heat exchange layer.

In a nineteenth aspect of the present disclosure, which may be used with the twelfth aspect in combination with any other aspect listed herein, at least one of the liquid inlet and liquid outlet terminates with an angled cut inside the thermal pad to prevent loss of liquid flow when the thermal pad bent or kinked.

In a twentieth aspect of the present disclosure, which may be used with the twelfth aspect in combination with any other aspect listed herein, the layers are sealed together at a plurality of spots within a border of the pad, the spots spaced apart to enable a desirable flowrate through the pad.

In a twenty-first aspect of the present disclosure, which may be used with the twentieth aspect in combination with any other aspect listed herein, the spots are spaced apart from each other by at least 0.5 in (12.7 mm).

In a twenty-second aspect of the present disclosure, which may be used with the twelfth aspect in combination with any other aspect listed herein, an outer surface of the outer layer includes a hook or pile material.

In a twenty-third aspect of the present disclosure, which may be used with the twenty-second aspect in combination with any other aspect listed herein, the therapy pad includes a strap that extends around the pad, one end of the strap securing to the hook or pile material of the outer surface of the outer layer, the opposing end of the strap securing to the strap itself.

In a twenty-fourth aspect of the present disclosure, which may be used with the twelfth aspect in combination with any other aspect listed herein, an inner surface of the inner layer includes a soft finish.

In a twenty-fourth aspect of the present disclosure, any of the structure and functionality illustrated and described above in connection with FIGS. 1 to 4 may be used in any combination with each other and with any of the other aspects listed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A cold therapy system comprising:
 a cooling bath structured to chill and hold chilled water;
 a pump positioned and arranged to pump the chilled water;
 a to-pad line positioned and arranged to hold chilled water pumped by the pump from the cooling bath;
 a from-pad line positioned and arranged to hold water returning to the cooling bath; and
 a therapy pad in fluid communication with the to- and from-pad lines, the therapy pad including a patient-contacting chamber and a chilled-water chamber residing outside of the patient-contacting chamber when the therapy pad is donned, the patient-contacting chamber in fluid communication and heat exchange communication with the chilled-water chamber.

2. The cold therapy system of claim 1, wherein the pump is located inside the cooling bath.

3. The cold therapy system of claim 1, wherein the to-pad line and the from-pad line are run together from the cooling bath to the therapy pad.

4. The cold therapy system of claim 1, which includes a flow restrictor placed in the from-pad line.

5. The cold therapy system of claim 4, wherein the flow restrictor is variable.

6. The cold therapy system of claim 5, wherein the flow restrictor is manually variable.

7. The cold therapy system of claim 4, wherein the flow restrictor is positioned at the cooling bath end of the from-pad line.

8. The cold therapy system of claim 1, wherein the to-pad line is placed in fluid communication with the chilled water chilled-water chamber and the from-pad line is placed in fluid communication with the patient-contacting chamber.

9. A cold therapy system comprising:
 a cooling bath structured to chill and hold chilled water;
 a pump positioned and arranged to pump the chilled water;
 a to-pad line positioned and arranged to hold chilled water pumped by the pump from the cooling bath;
 a from-pad line positioned and arranged to hold water returning to the cooling bath; and
 a therapy pad in fluid communication with the to- and from-pad lines, the therapy pad including a patient-contacting chamber and a chilled-water chamber, the patient-contacting chamber in fluid communication and heat exchange communication with the chilled-water chamber, the volume of the therapy pad when inflated having a ratio to a volume of liquid that is pumped by the pump through the therapy pad over one minute of at least 1:1.

10. The cold therapy system of claim 9, wherein the volume of the therapy pad when inflated compared to the volume of the liquid that is pumped by the pump through the therapy pad over one minute is within a range of 1:1 to 2.5:1.

11. The cold therapy system of claim 9, wherein the heat exchange communication is a countercurrent heat exchange communication.

12. A therapy pad for a cold therapy system comprising:
 an outer layer;
 an inner layer;
 a middle heat exchange layer;
 a liquid inlet; and
 a liquid outlet,
 wherein the layers are sealed together such that the outer layer and the middle heat exchange layer form a chilled-water chamber, the inner layer and the middle heat exchange layer form a patient-contacting chamber in fluid communication with the chilled-water chamber, the liquid inlet is in sealed communication with the chilled-water chamber, and the liquid outlet is in sealed communication with the patient-contacting chamber.

13. The thermal pad of claim 12, wherein the middle heat exchange layer is at least half as thin as at least one of the inner or outer layers.

14. The thermal pad of claim 12, wherein the middle heat exchange layer is equal to or less than 0.007 inch (0.18 mm) thick.

15. The thermal pad of claim 12, wherein the layers are further sealed together so as to form a first serpentine flowpath in the chilled-water chamber and a second serpentine flowpath in the patient-contacting chamber.

16. The thermal pad of claim 15, wherein the first serpentine flowpath matches, at least substantially, the second serpentine flowpath.

17. The thermal pad of claim 15, wherein the middle heat exchange layer forms an aperture that enables an outlet end of the first serpentine flowpath to communicate with an inlet end of the second serpentine flowpath.

18. The thermal pad of claim 12, wherein the liquid inlet includes a first tube sealed to a chilled-water side of the middle heat exchange layer and the liquid outlet includes a second tube sealed to a patient-contacting side of the middle heat exchange layer.

19. The thermal pad of claim 12, wherein at least one of the liquid inlet and liquid outlet terminates with an angled cut inside the thermal pad to prevent loss of liquid flow when the thermal pad is bent or kinked.

20. The thermal pad of claim 12, wherein the layers are sealed together at a plurality of spots within a border of the pad, the spots spaced apart to enable a desirable flowrate through the pad.

21. The therapy pad of claim 20, wherein the spots are spaced apart from each other by at least 0.5 in (12.7 mm).

22. The therapy pad of claim 12, wherein an outer surface of the outer layer includes a hook or pile material.

23. The therapy pad of claim 22, which includes a strap that extends around the pad, one end of the strap securing to the hook or pile material of the outer surface of the outer layer, the opposing end of the strap securing to the strap itself.

24. The therapy pad of claim 12, wherein an inner surface of the inner layer includes a soft finish.

* * * * *